United States Patent
Li et al.

(10) Patent No.: US 10,890,560 B2
(45) Date of Patent: Jan. 12, 2021

(54) FORMING NANOSCALE PORES IN A SEMICONDUCTOR STRUCTURE UTILIZING NANOTUBES AS A SACRIFICIAL TEMPLATE

(71) Applicant: International Business Machines Corporation, Armonk, NY (US)

(72) Inventors: Juntao Li, Cohoes, NY (US); Kangguo Cheng, Schenectady, NY (US); Peng Xu, Santa Clara, CA (US); Zhenxing Bi, Schenectady, NY (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 15/985,266

(22) Filed: May 21, 2018

(65) Prior Publication Data
US 2019/0353615 A1 Nov. 21, 2019

(51) Int. Cl.
*G01N 27/447* (2006.01)
*B82B 3/00* (2006.01)
(Continued)

(52) U.S. Cl.
CPC ....... *G01N 27/44791* (2013.01); *B82B 1/001* (2013.01); *B82B 1/005* (2013.01);
(Continued)

(58) Field of Classification Search
CPC .. G01N 27/44791; B82B 1/001; B82B 1/004; B82B 1/005; B82B 3/0014; B82B 3/008; B82B 3/0019
See application file for complete search history.

(56) References Cited

U.S. PATENT DOCUMENTS

| 7,276,389 B2 | 10/2007 | Kim et al. |
| 7,625,469 B1 * | 12/2009 | Yelton ................. G01N 27/403 204/194 |

(Continued)

FOREIGN PATENT DOCUMENTS

WO    2016049657 A1    3/2016

OTHER PUBLICATIONS

M.P. Siegal et al., "Precise Control of Multiwall Carbon Nanotube Diameters Using Thermal Chemical Vapor Deposition," Applied Physics Letters, Mar. 25, 2002, pp. 2171-2173, vol. 80, No. 12.

(Continued)

*Primary Examiner* — Brigitte A Paterson
(74) *Attorney, Agent, or Firm* — Randall Bluestone; Ryan, Mason & Lewis, LLP (57) ABSTRACT

A method of forming a semiconductor structure includes forming two or more catalyst nanoparticles from a metal layer disposed over a substrate in two or more openings of a hard mask patterned over the metal layer. The method also includes growing two or more carbon nanotubes using the catalyst nanoparticles, and removing the carbon nanotubes to form two or more nanoscale pores. The two or more nanoscale pores may be circular nanoscale pores having a substantially uniform diameter. The two or more openings in the hard mask may have non-uniform size, and the substantially uniform diameter of the two or more nanopores may be controlled by a size of the carbon nanotubes.

18 Claims, 12 Drawing Sheets

(51) Int. Cl.
*G01N 33/487* (2006.01)
*B82B 1/00* (2006.01)
*B82Y 40/00* (2011.01)
*B82Y 15/00* (2011.01)

(52) U.S. Cl.
CPC ............ *B82B 3/008* (2013.01); *B82B 3/0014* (2013.01); *B82B 3/0019* (2013.01); *G01N 33/48721* (2013.01); *B82Y 15/00* (2013.01); *B82Y 40/00* (2013.01)

(56) References Cited

U.S. PATENT DOCUMENTS

| | | | |
|---|---|---|---|
| 8,093,628 | B2 | 1/2012 | Yang et al. |
| 8,828,138 | B2 | 9/2014 | Bedell et al. |
| 8,890,121 | B1 | 11/2014 | Han et al. |
| 8,900,975 | B2 | 12/2014 | Chang et al. |
| 8,945,404 | B2 | 2/2015 | Afzali-Ardakani et al. |
| 8,986,980 | B2 | 3/2015 | Stolovitzky et al. |
| 2012/0193235 | A1 | 8/2012 | Afzali-Ardakani et al. |
| 2015/0028845 | A1 | 1/2015 | Zhu |
| 2015/0056407 | A1 | 2/2015 | Astier et al. |
| 2015/0170990 | A1* | 6/2015 | Tseng ................. H01L 21/4871 257/712 |
| 2017/0349940 | A1 | 12/2017 | Morin et al. |
| 2017/0356038 | A1* | 12/2017 | So .......................... B32B 37/18 |

OTHER PUBLICATIONS

S. Sato et al., "Growth of Diameter-Controlled Carbon Nanotubes Using Monodisperse Nickel Nanoparticles Obtained with a Differential Mobility Analyzer," Chemical Physics Letters, Dec. 5, 2003, pp. 361-366, vol. 382, No. 3-4.

H. Qi et al., "Synthesis of Uniform Double-Walled Carbon Nanotubes Using Iron Dislicide as Catalyst," Nano Letters, Aug. 7, 2007, pp. 2417-2421, vol. 7, No. 8.

* cited by examiner

FORMING NANOSCALE PORES IN A SEMICONDUCTOR STRUCTURE UTILIZING NANOTUBES AS A SACRIFICIAL TEMPLATE

BACKGROUND

The present application relates to semiconductors, and more specifically, to techniques for forming semiconductor structures. Semiconductor structures including nanoscale pores, also referred to as nanopores, may be used for molecule detection. A semiconductor structure including a nanopore may be immersed in a conducting fluid with an electric potential or voltage applied across the nanopore. Detection of electrical current due to conduction of ions through the nanopore can thus be measured. If individual molecules or particles pass through the nanopore, this can create a change in the magnitude of the current through the nanopore. The measured change in magnitude of the current may be related to particular types of molecules for detection, possibly in combination with other types of electrical or optical sensors placed around the nanopore.

SUMMARY

Embodiments of the invention provide techniques for forming nanoscale pores in semiconductor structures.

In one embodiment, a method of forming a semiconductor structure comprises forming two or more catalyst nanoparticles from a metal layer disposed over a substrate in two or more openings of a hard mask patterned over the metal layer, growing two or more carbon nanotubes using the catalyst nanoparticles, and removing the carbon nanotubes to form two or more nanoscale pores.

In another embodiment, a semiconductor structure comprises a substrate, an insulator disposed over the substrate, a metal layer disposed over the substrate, a hard mask disposed over the metal layer, the hard mask and the metal layer having two or more patterned openings, inner sidewall spacers disposed on sidewalls of the metal layer and the hard mask in the patterned openings, an oxide layer disposed over the hard mask and filling the patterned openings, and two or more nanoscale pores disposed in the oxide layer in the patterned openings.

In another embodiment, a nanoscale pore-based molecule detection device comprises a chamber comprising a conductive solution, first and second electrochemical electrodes in contact with the conductive solution and coupled to a voltage source, and a semiconductor structure disposed in the chamber. The semiconductor structure comprises a substrate, an insulator disposed over the substrate, a metal layer disposed over the substrate, a hard mask disposed over the metal layer, the hard mask and the metal layer having two or more patterned openings, inner sidewall spacers disposed on sidewalls of the metal layer and the hard mask in the patterned openings, an oxide layer disposed over the hard mask and filling the patterned openings, and two or more nanoscale pores disposed in the oxide layer in the patterned openings.

DETAILED DESCRIPTION

Illustrative embodiments of the invention may be described herein in the context of illustrative methods for forming nanoscale pores in semiconductor structures, along with apparatus, systems and devices formed using such methods. However, it is to be understood that embodiments of the invention are not limited to the illustrative methods, apparatus, systems and devices but instead are more broadly applicable to other suitable methods, apparatus, systems and devices.

Nanoscale pores, also referred to herein as nanopores, have a wide variety of applications. For example, nanopore-based devices may be used for deoxyribonucleic acid (DNA) sequencing. A nanopore-based DNA sequencing device may provide single-molecule detection or analytical capabilities that are achieved by driving molecules in a solution through nanopores. As single bases or strands of DNA pass (or as a part of a DNA molecule passes) through a nanopore, it can create a change in the magnitude of the current through the nanopore. DNA may be driven through the nanopore using various methods, such as through the use of an electric field to attract DNA towards one or more nanopores. The scale or size of the nanopore can advantageously force the DNA through the nanopore hole as a long string (e.g., one base at a time) permitting DNA sequence detection.

Current lithography techniques, however, have limitations for forming ultra-small pores with uniform circular shapes and size distribution. Nanopores of specific sizes (e.g., uniformly sized circular nanopores) may be required for certain nanopore-based DNA sequencing or other particle or molecule detection devices, as specific size nanopores are need to allow particular molecules of interest to pass through the nanopores. Therefore, there is a need for techniques for forming highly ordered nanopores in semiconductor structures.

Illustrative embodiments provide techniques for forming circular nanopores using nanotubes as sacrificial templates, thus achieving formation of uniformly sized nanopores in a semiconductor structure. In some embodiments, nanopores are formed with diameters of 5 nanometers (nm) or less. Advantageously, illustrative embodiments are immune to critical dimension (CD) variation resulting from initial via CD variations.

Figure 1:
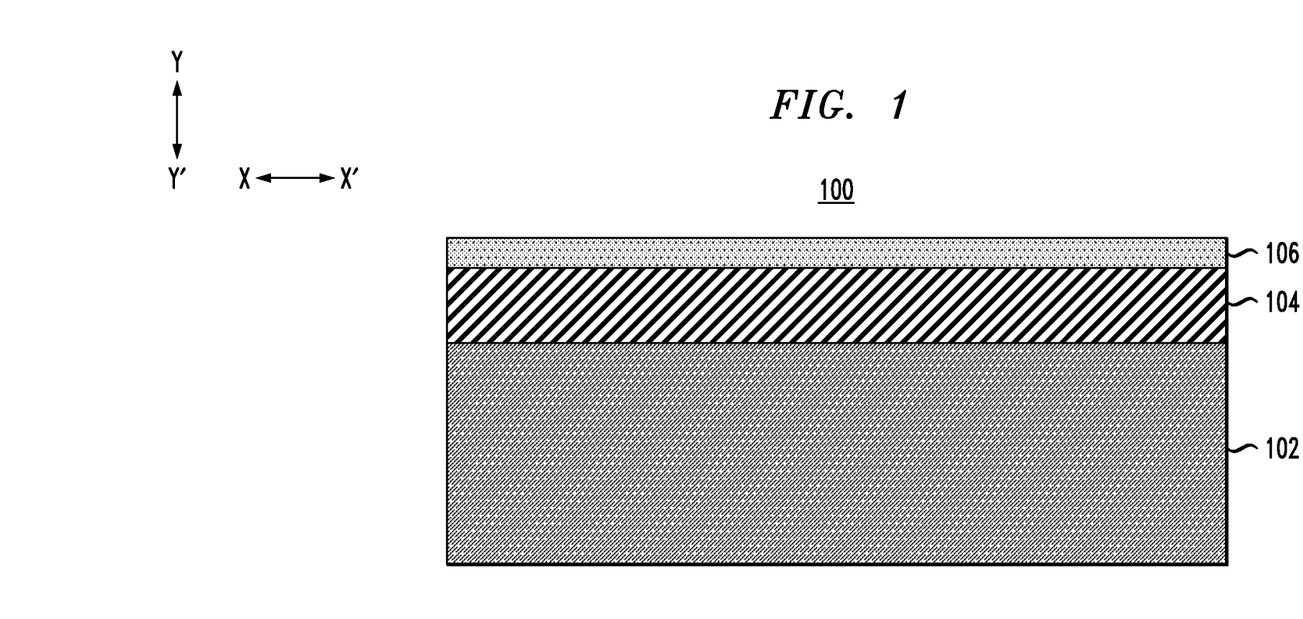
FIG. 1 depicts a cross-sectional view of a semiconductor structure including a metal layer deposited over a substrate, according to an embodiment of the present invention.

A process for forming nanopores will now be described with respect to FIGS. 1-9. FIG. 1 shows a side cross-sectional view 100 of a semiconductor structure including a substrate 102, an oxide or insulator 104 formed over the substrate, and a thin metal layer 106 deposited over the oxide 104.

The substrate 102 may include one or more semiconductor materials. Non-limiting examples of substrate 102 materials include silicon (Si), strained Si, silicon carbide (SiC), germanium (Ge), silicon germanium (SiGe), silicon-germanium-carbon (SiGeC), Si alloys, Ge alloys, gallium arsenide (GaAs), indium arsenide (InAs), indium phosphide (InP), or any combination thereof. Other examples of suitable substrates 102 include silicon-on-insulator (SOI) and silicon-germanium-on-insulator (SGOI) substrates with buried oxide (BOX) layers. The substrate may also contain isolations and transistors. The insulator 104 may be formed of an oxide or other suitable material such as silicon nitride (SiN), silicoboron carbonitride (SiBCN), silicon carbonitride (SiCN), silicon carbon oxynitride (SiCON), or any other type of dielectric material. The insulator 104 may have a vertical thickness (in direction Y-Y') ranging from 10 nm to 200 nm.

The metal layer 106 may be formed of gold (Au) or another suitable material such as nickel (Ni), iron (Fe), a nickel-iron alloy (Ni-Fe), platinum (Pt), cobalt (Co), alloys of two or more of Ni, Fe, Pt, Co, etc. The metal layer 106 may be deposited using various techniques, including but not limited to physical vapor deposition (PVD), chemical vapor deposition (CVD), atomic layer deposition (ALD), molecular beam epitaxy (MBE), or any of the various modifications thereof, with a vertical thickness (in direction Y-Y') of 2 nm, or more generally a vertical thickness in the range of 0.5 nm to 5 nm.

Figure 2:
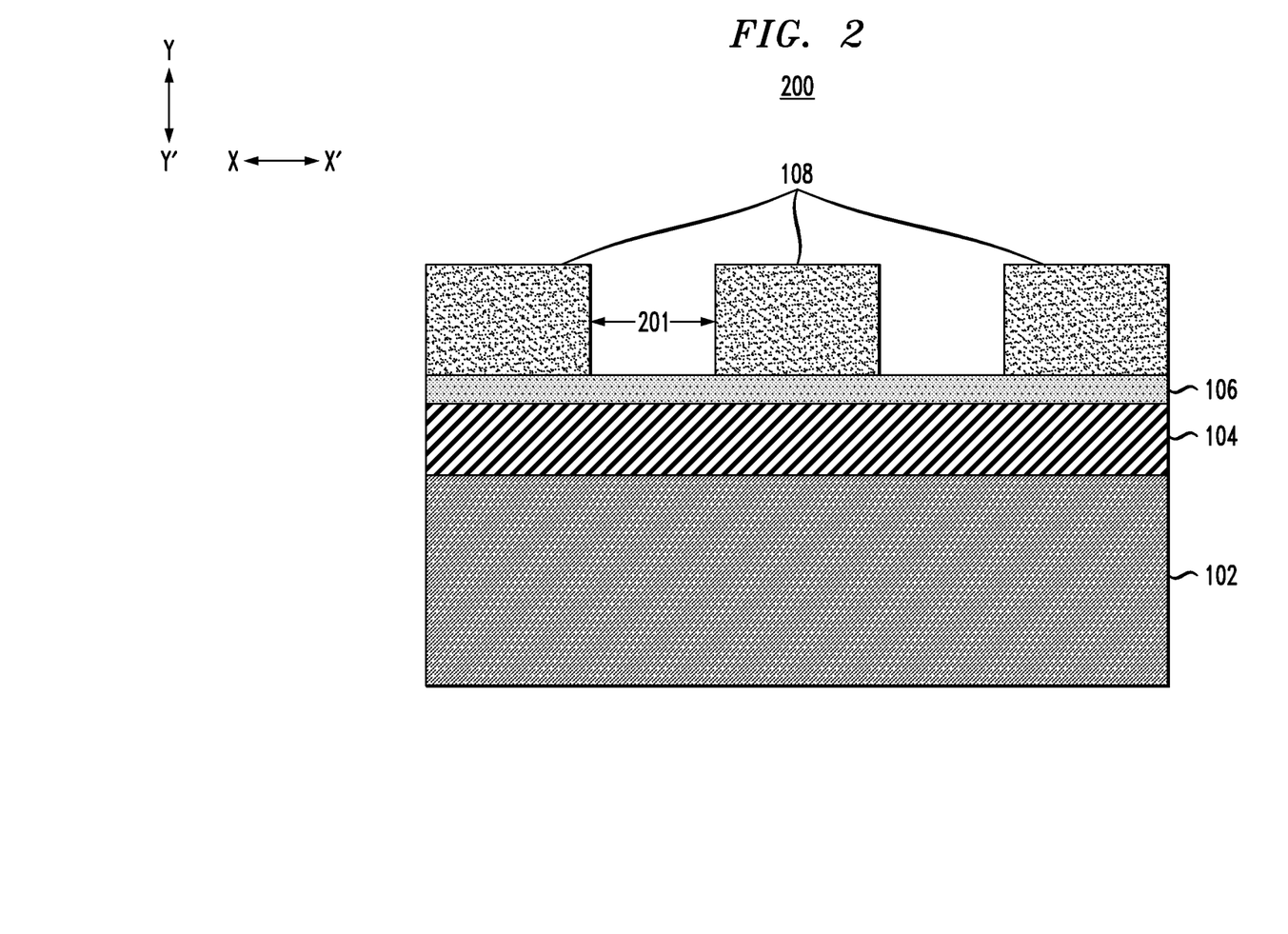
FIG. 2 depicts a cross-sectional view of the FIG. 1 semiconductor structure following patterning a hard mask over the metal layer, according to an embodiment of the present invention.

FIG. 2 shows a side cross-sectional view 200 of the FIG. 1 structure following patterning of a hard mask 108 over the metal layer 106. The hard mask 108 may be formed of an oxide or other suitable material such as silicon oxide ($SiO_2$), silicon carbide (SiC), silicon nitride ($Si_3N_4$), etc. The hard mask 108 may have a vertical thickness (in direction Y-Y') ranging from 20 nm to 100 nm. The material of the hard mask 108 may initially be formed over the entire surface of metal layer 106, followed by patterning of a suitable resist material, etching of exposed portions of the hard mask material and removal of the resist to form the patterned hard mask 108 pads shown in FIG. 2. In some embodiments, a gap 201 between the patterned hard mask 108 pads is 10 nm, or more generally in the range of 10 nm to 50 nm.

Due to process variation, the initial size of the gaps between the patterned hard mask 108 pads may vary, thus there are non-uniform "vias" formed in the spaces between the patterned hard mask 108 pads. These "vias" may end up with various CD, such as ±2 nm, and thus the gap 201 between the patterned hard mask 108 pads may vary between 8 and 12 nm. Illustrative embodiments are immune to this CD variation, as will be described in further detail below, as the final nanopores which are formed are defined by carbon nanotube templates.

Figure 3:
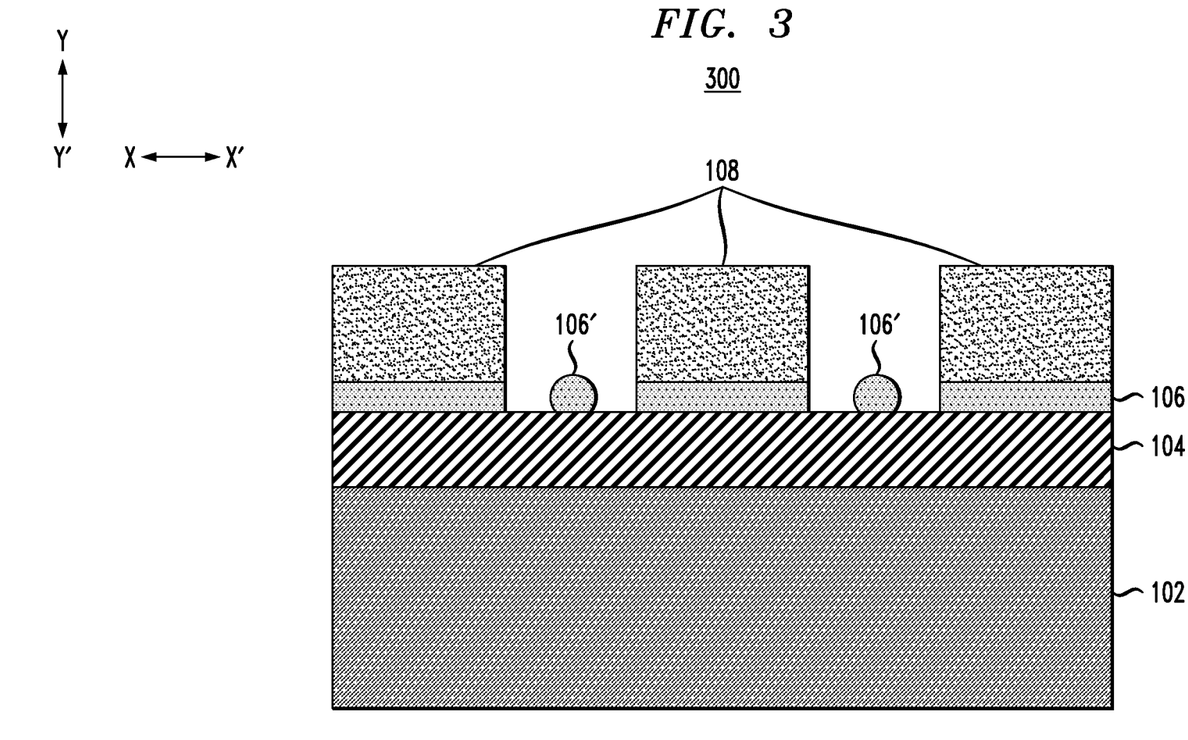
FIG. 3 depicts a cross-sectional view of the FIG. 2 semiconductor structure following an anneal to form catalyst nanoparticles from the metal layer, according to an embodiment of the present invention.

FIG. 3 shows a side cross-sectional view 300 of the FIG. 2 structure following an anneal process, which forms catalyst nanoparticles 106' from the metal layer 106 in regions exposed by the patterned hard mask 108. The anneal may be a thermal anneal. The temperature at which annealing is performed depends on the thickness of the metal layer 106 and the material used in the metal layer 106. In some embodiments, the thermal anneal is performed at a temperature between 500° C. and 800° C. in an inert atmosphere, for a duration in the range of a few seconds to hours. More generally, the thermal anneal is at a temperature and duration sufficient to cause the exposed portions of the metal layer 106 to melt and agglomerate into the catalyst nanoparticles 106'. Each of the catalyst nanoparticles 106' may have a horizontal width (in direction X-X') ranging from 2 nm to 5 nm and a vertical thickness (in direction Y-Y') ranging from 2 nm to 5 nm.

Figure 4:
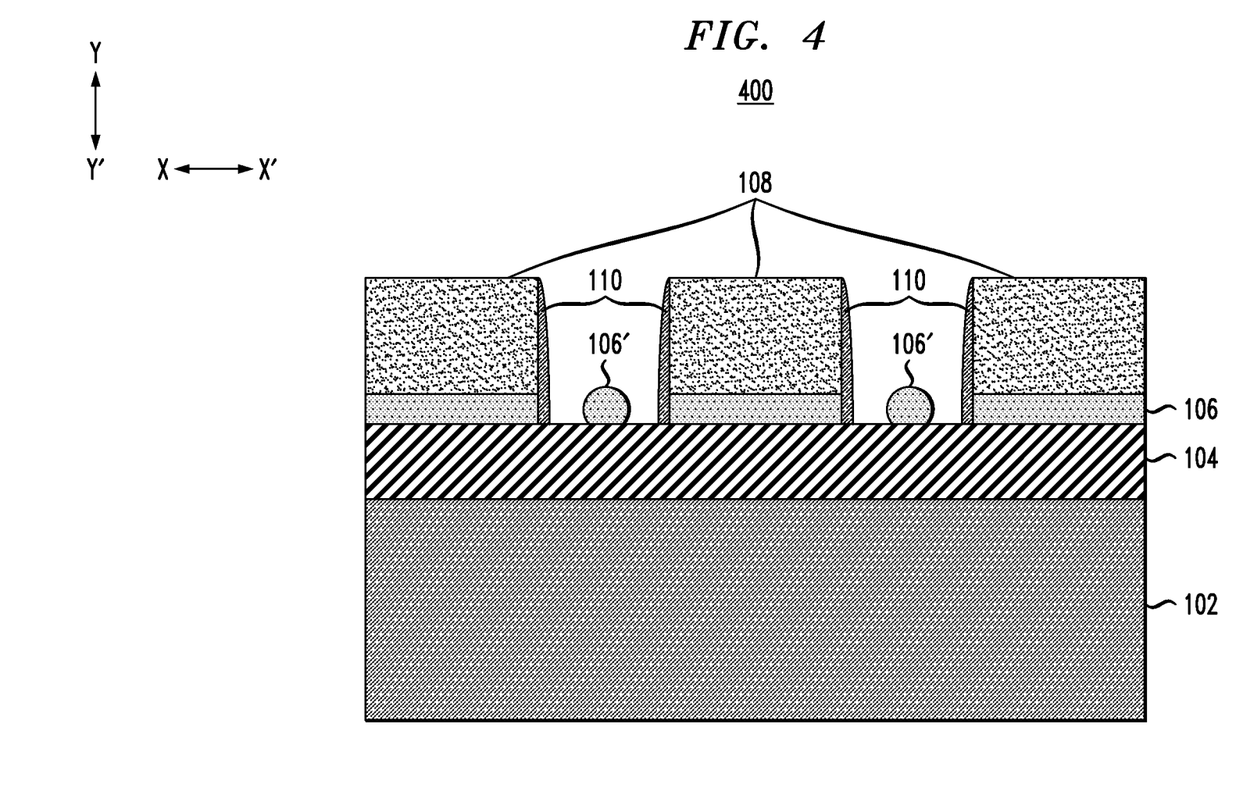
FIG. 4 depicts a cross-sectional view of the FIG. 3 semiconductor structure following formation of an inner sidewall spacer, according to an embodiment of the present invention.

FIG. 4 depicts a side cross-sectional view 400 of the FIG. 3 structure following formation of inner sidewall spacers 110. The inner sidewall spacers 110 cover the exposed portions of the remaining metal layer 106, and further shrink the CD of the "vias" or gaps between the patterned hard mask 108. The inner sidewall spacers 110 may be formed using sidewall image transfer (SIT) or other suitable techniques. The inner sidewall spacers 110 may be formed of silicon nitride (SiN), silicon oxide ($SiO_x$), silicon carbide (SiC), or another suitable material. As shown, the inner sidewall spacers 110 may have a horizontal width (in direction X-X') that varies from a widest point proximate a top surface of oxide 104 and narrows towards a top surface of the patterned hard mask 108. The horizontal width at the widest point may be in the range of 5 nm to 20 nm, with the horizontal width at the narrowest point being in the range of 1 nm to 5 nm.

Figure 5:
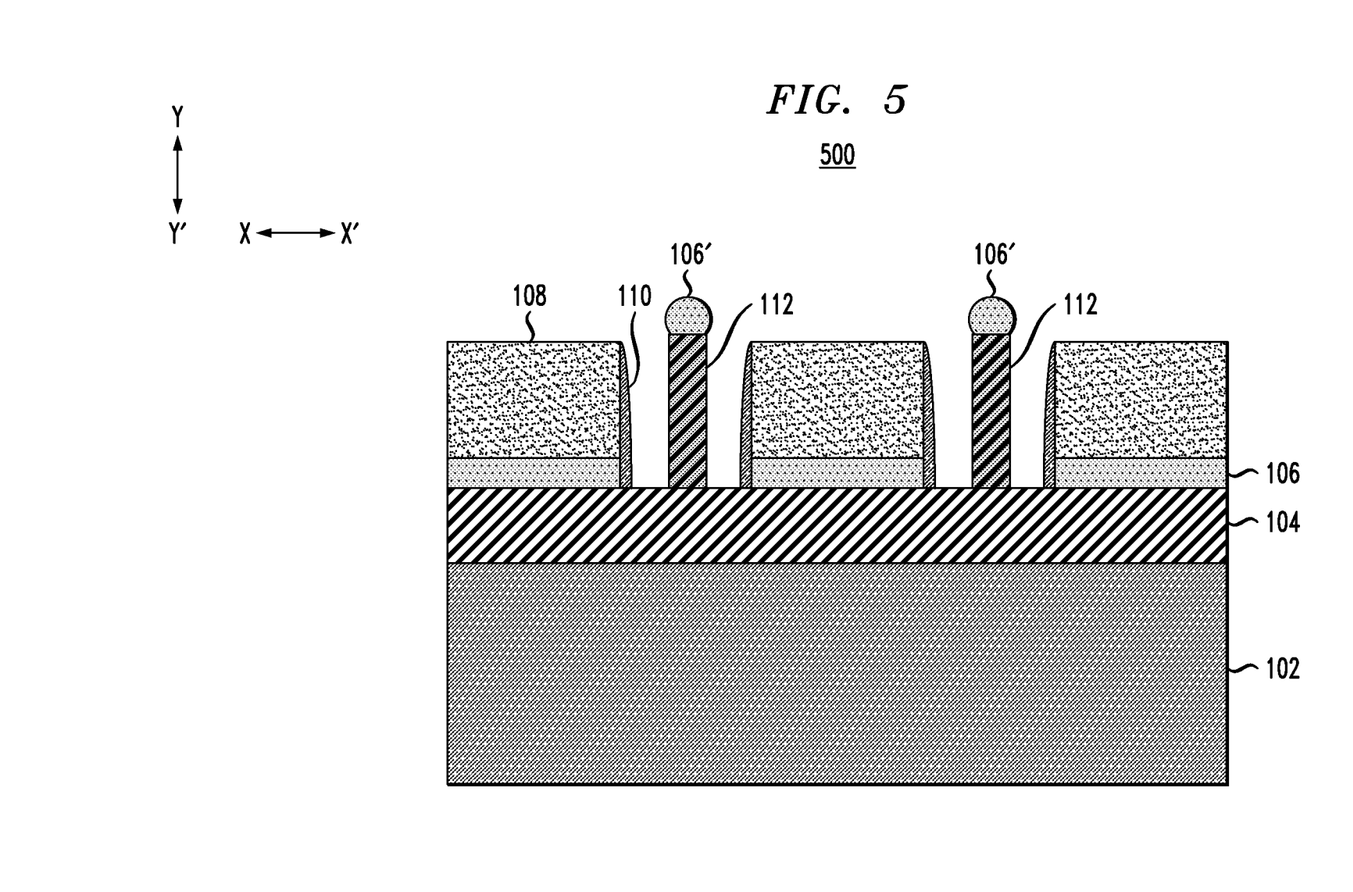
FIG. 5 depicts a cross-sectional view of the FIG. 4 semiconductor structure following growth of carbon nanotubes, according to an embodiment of the present invention.

FIG. 5 shows a side cross-sectional view 500 of the FIG. 4 structure following growth of carbon nanotubes 112. The carbon nanotubes 112 are grown using the catalyst nanoparticles 106', and thus the size of the carbon nanotubes 112 is controlled by the size of the catalyst nanoparticles 106'. In some embodiments, the carbon nanotubes are grown using a tip-growth model, where a hydrocarbon precursor molecule decomposes on the top surface of the catalyst metal particle (e.g., catalyst nanoparticles 106'). Carbon diffuses down through the catalyst metal, and the carbon nanotube precipitates out across the metal bottom, pushing the whole metal particle off the substrate (e.g., the top surface of insulator 104) due to the weak catalyst-substrate interaction. The carbon nanotube continues to grow as long as the metal's top is open for incoming hydrocarbon molecule decomposition. Growth of the carbon nanotube is stopped once the metal is fully covered with excess carbon.

Figure 6:
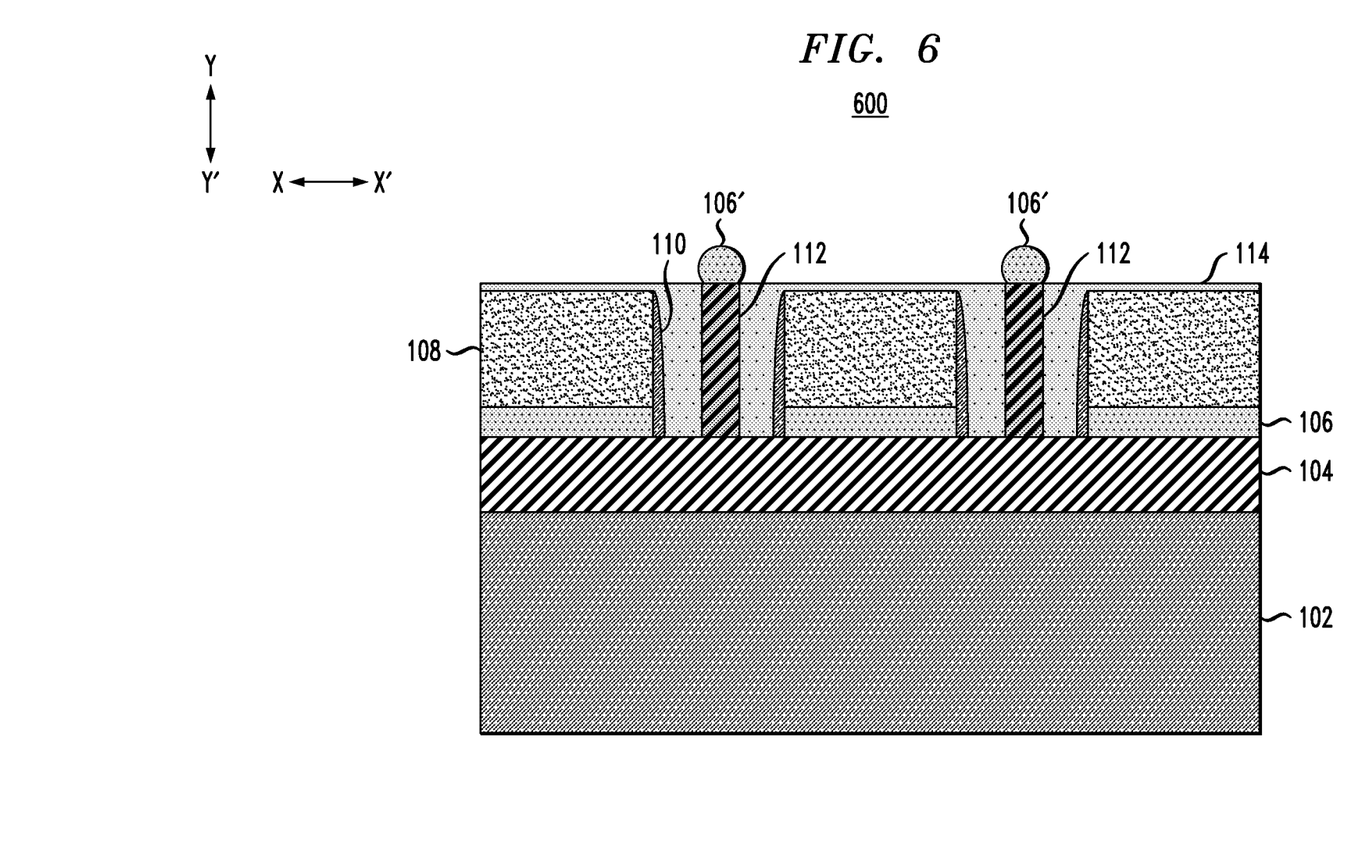
FIG. 6 depicts a cross-sectional view of the FIG. 5 semiconductor structure following fill and recess of an oxide, according to an embodiment of the present invention.

FIG. 6 shows a side cross-sectional view 600 of the FIG. 5 structure following fill and recess of an oxide 114. The oxide 114 is initially filled to cover the entire structure, and is then recessed to expose the catalyst nanoparticles 106'.

Figure 7:
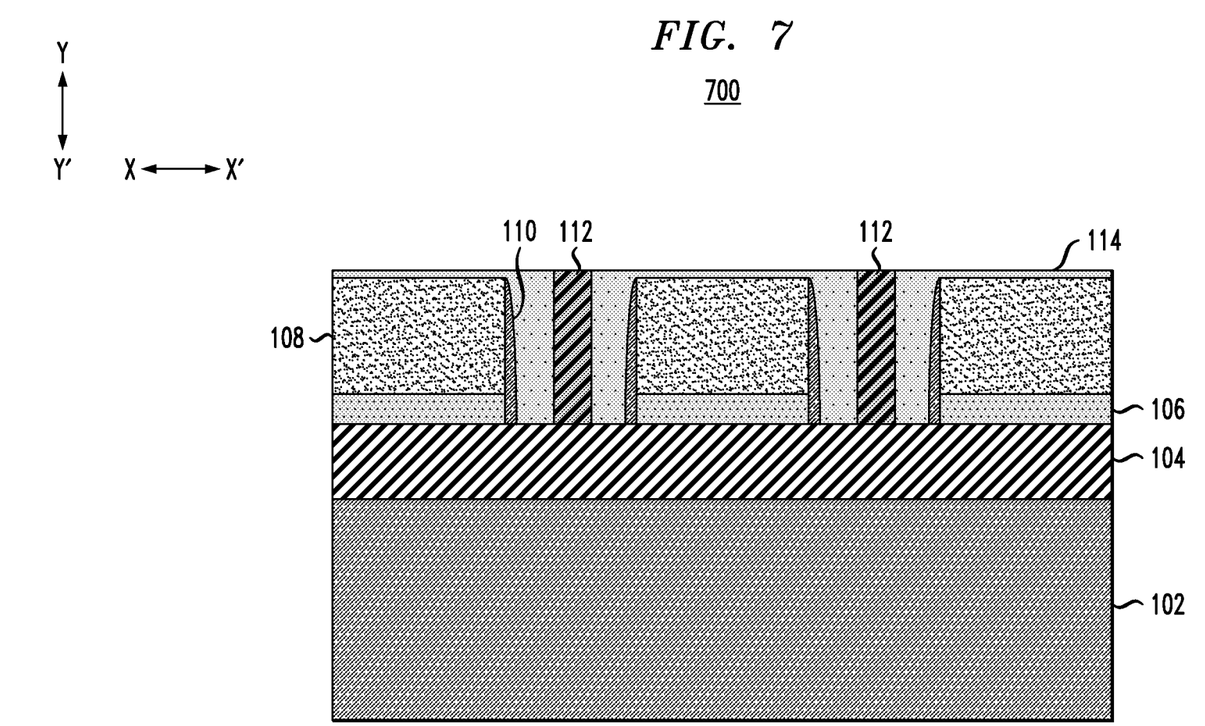
FIG. 7 depicts a cross-sectional view of the FIG. 6 semiconductor structure following removal of the catalyst nanoparticles, according to an embodiment of the present invention.

FIG. 7 shows a side cross-sectional view 700 of the FIG. 6 structure following removal of the catalyst nanoparticles

106'. The catalyst nanoparticles 106' may be removed using a suitable wet and/or dry etch process that depends on the material type of the catalyst nanoparticles 106'. For example, if the catalyst nanoparticles 106' are Au, the wet etch may be nitric acid ($HNO_3$).

Figure 8:
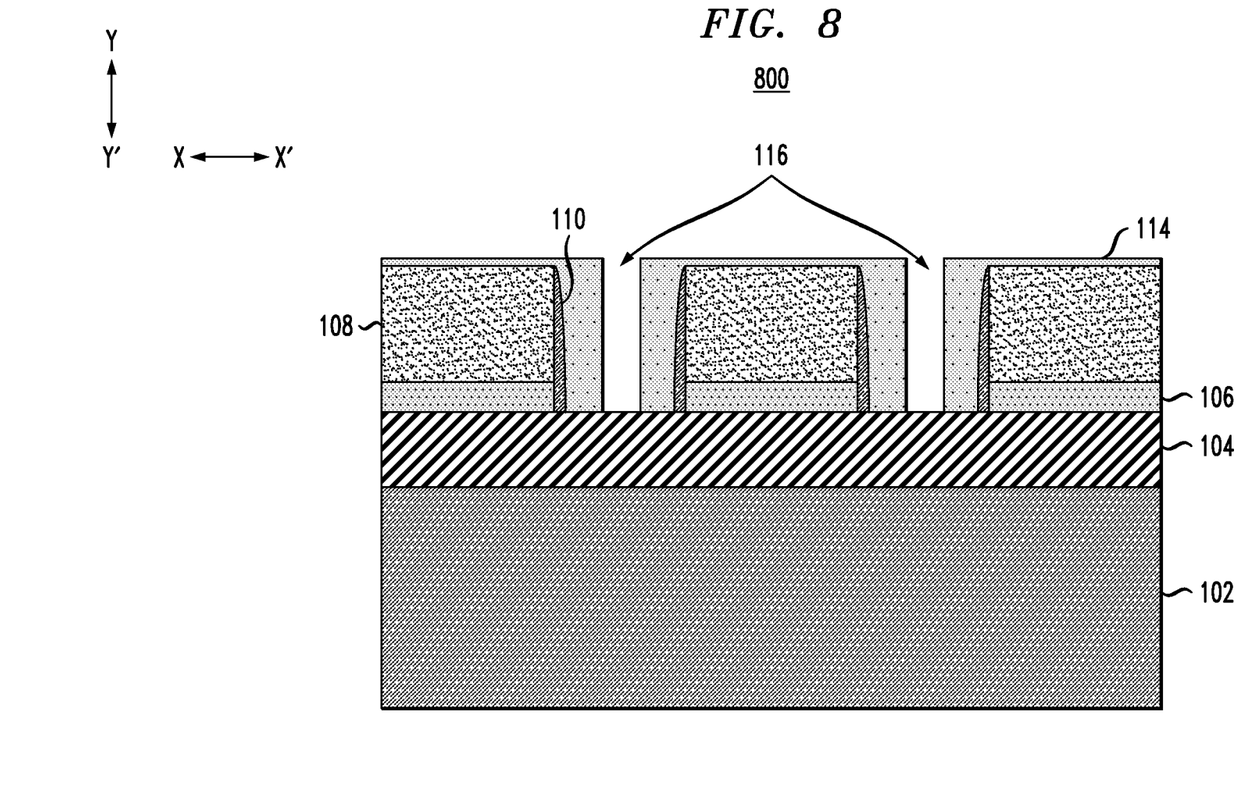
FIG. 8 depicts a cross-sectional view of the FIG. 7 semiconductor structure following etching of the carbon nanotubes, according to an embodiment of the present invention.

FIG. 8 shows a side cross-sectional view 800 of the FIG. 7 structure following etching of the carbon nanotubes 112 to form nanopores 116. The carbon nanotubes 112 may be etched using, for example, ozone or another suitable etch process such as water-assisted etching. Advantageously, the resulting nanopores 116 are uniformly sized as defined by the diameter of the carbon nanotubes 112 and are immune to original variation in the CD of the vias or gaps between the patterned hard mask 108. Further, the nanopores 116 may be formed with a tight and uniform distribution and with sizes beyond the limits of lithography-based formation.

Figure 9A:
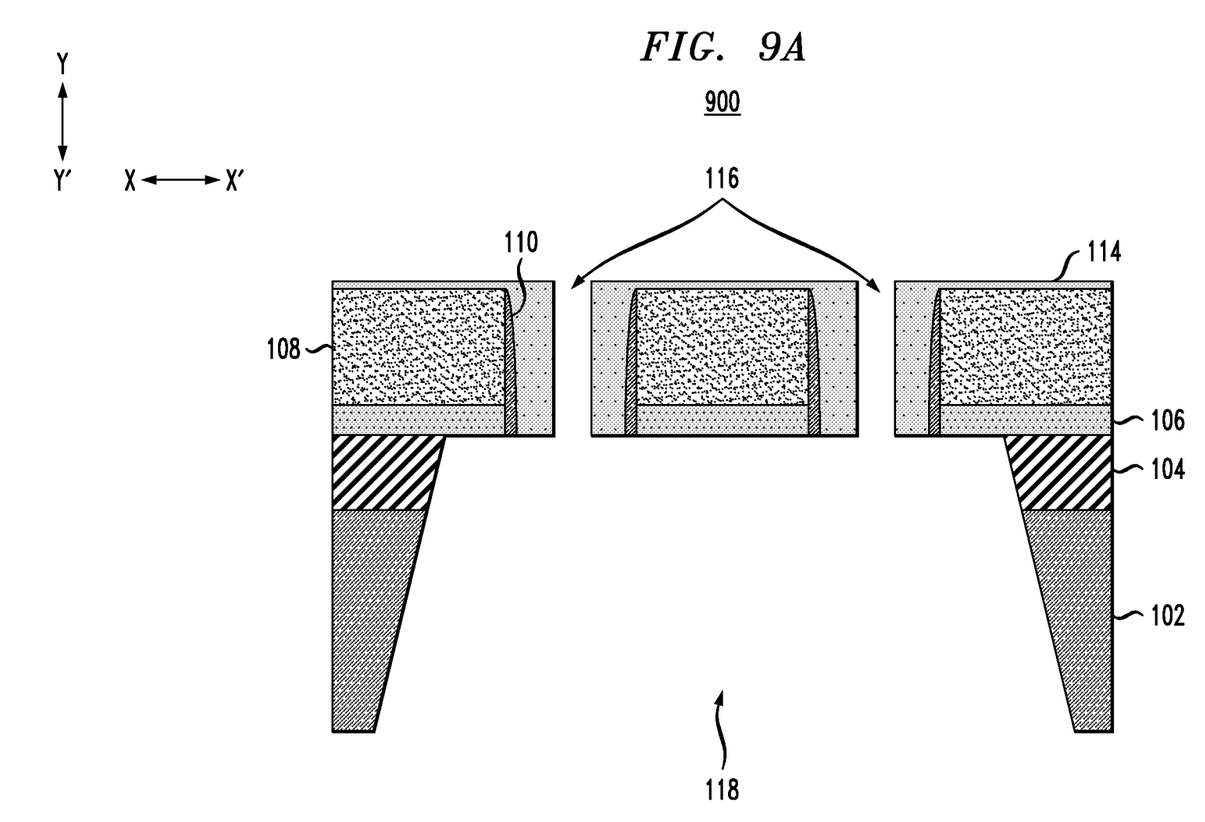
FIG. 9A depicts a cross-sectional view of the FIG. 8 semiconductor structure following formation of a back chamber in the substrate, according to an embodiment of the present invention.
Figure 9B:
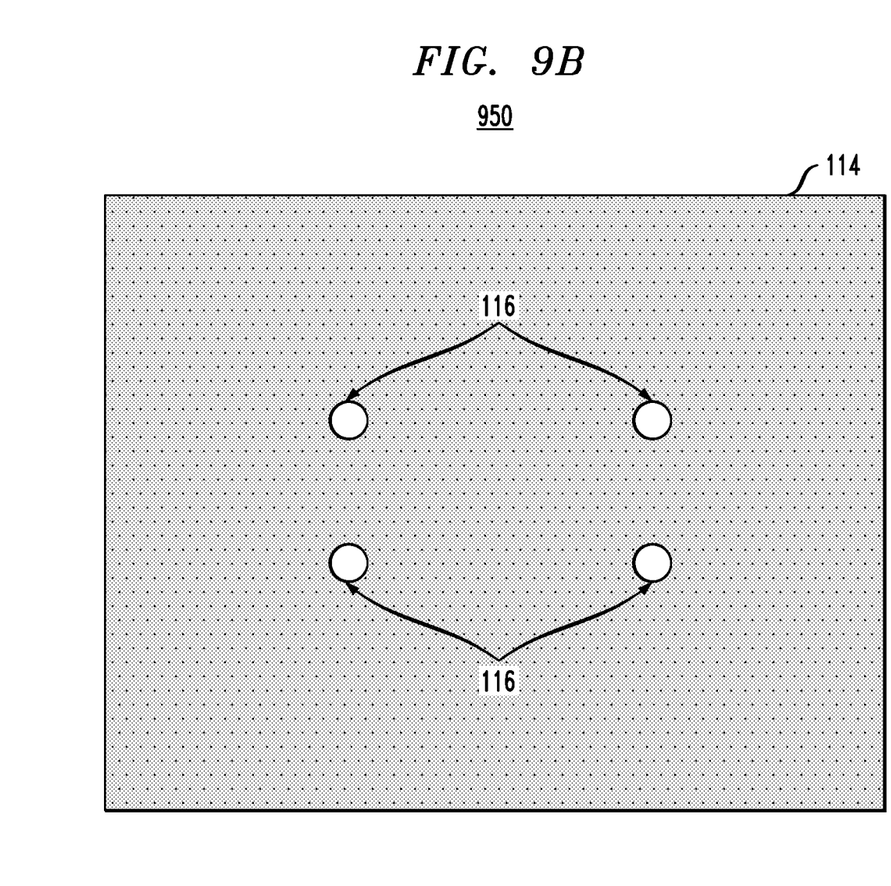
FIG. 9B depicts a top-down view of the FIG. 9A semiconductor structure, according to an embodiment of the present invention.

FIG. 9A shows a side cross-sectional view 900 of the FIG. 8 structure following formation of a back chamber 118 in the substrate 102 to expose the nanopores 116. The back chamber 118 may be formed using suitable processing, such as through wafer thinning, back side etching, etc. Any suitable patterning technique (e.g., photolithography followed by etching) can be used to form the chamber 118. FIG. 9B shows a top-down view 950 of the FIG. 9A structure, and FIG. 9C shows a bottom-up view 975 of the FIG. 9A structure, illustrating the tight distribution of nanopores 116.

Figure 9C:
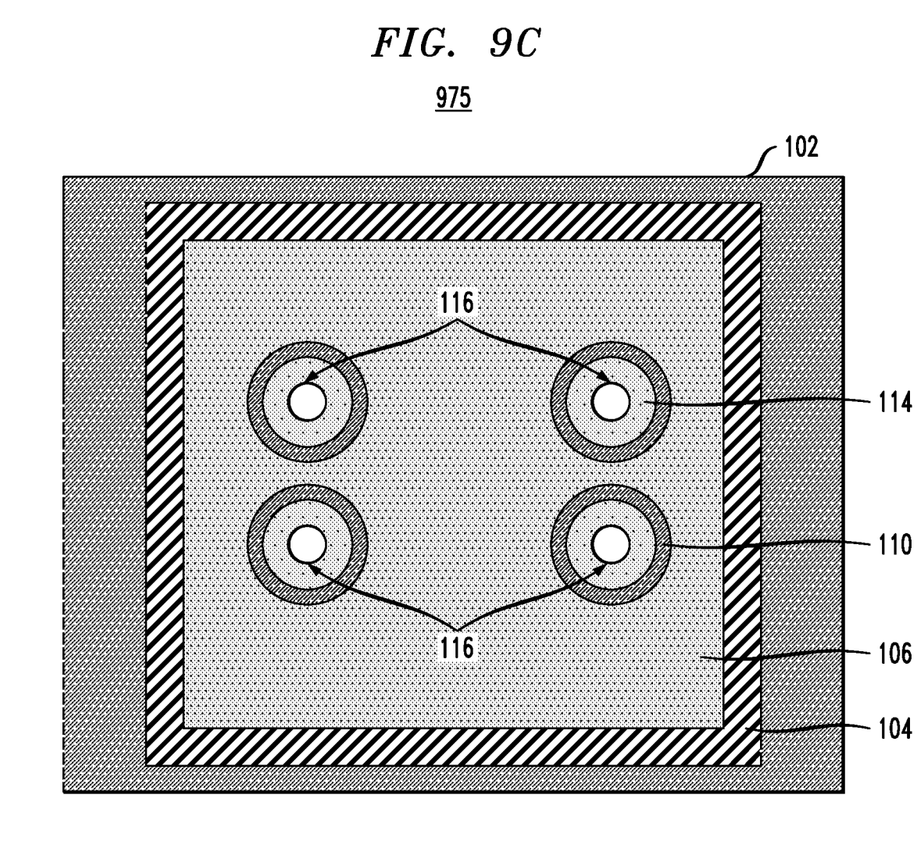
FIG. 9C depicts a bottom-up view of the FIG. 9A semiconductor structure, according to an embodiment of the present invention.
Figure 10:
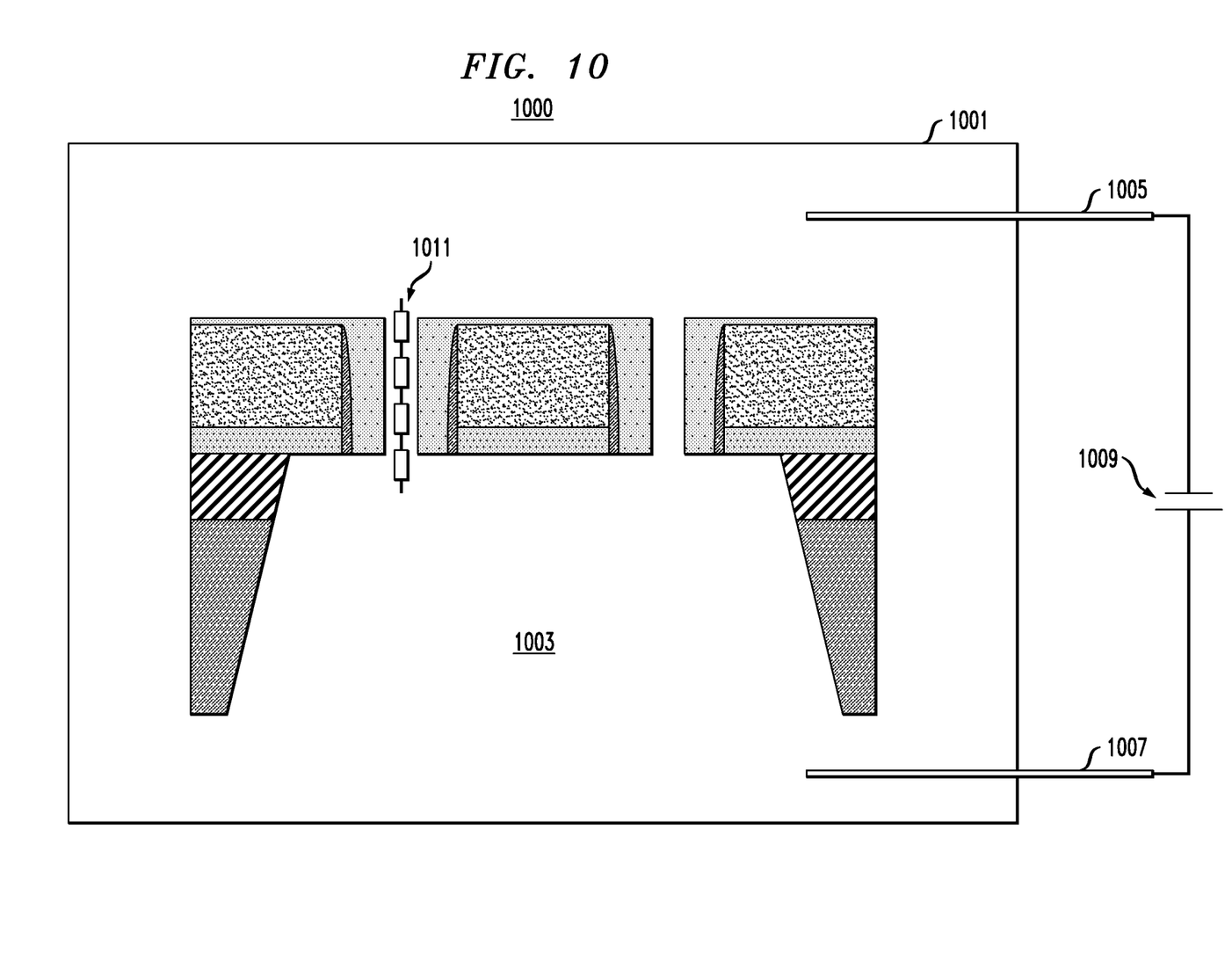
FIG. 10 depicts molecule detection utilizing the semiconductor structure of FIGS. 9A-9C, according to an embodiment of the present invention.

FIG. 10 depicts an example of molecule detection 1000 utilizing the structure of FIGS. 9A-9C. As shown, the structure of FIGS. 9A-9C is positioned in a chamber 1001 containing a conducting fluid 1003. An electrical voltage bias is provided by voltage source 1009 through electrochemical electrodes 1005 and 1007 placed in contact with different portions of the conducting fluid 1003 in chamber 1001 to measure a change in current caused by a molecule 1011 passing through one of the nanopores of the structure of FIGS. 9A-9C. In some embodiments, the molecule 1011 may be a DNA molecule (e.g., with bases shown in white rectangles connected via backbones shown by the solid line). By measuring the current, one can detect the DNA molecule when it passes through the nanopore. Other molecules, including but not limited to ribonucleic acid (RNA), amino acids, proteins, viruses, etc., can also be detected using this technique.

In some embodiments, a method of forming a semiconductor structure comprises forming two or more catalyst nanoparticles from a metal layer disposed over a substrate in two or more openings of a hard mask patterned over the metal layer, growing two or more carbon nanotubes using the catalyst nanoparticles, and removing the carbon nanotubes to form two or more nanoscale pores.

The two or more nanoscale pores may comprise circular nanoscale pores having a substantially uniform diameter. The two or more openings in the hard mask may have non-uniform size, and the substantially uniform diameter of the two or more nanopores may be controlled by a size of the carbon nanotubes. The substantially uniform diameter may be 5 nm or less.

The metal layer may comprise at least one of Au, Ni, Fe and a Ni—Fe alloy.

The substrate may comprise an insulator disposed over a semiconductor material.

The patterned hard mask may comprise a set of oxide pads with gaps between the oxide pads varying in a range of 8 to 12 nm.

Forming the catalyst nanoparticles may comprise performing a thermal anneal to form the catalyst nanoparticles from portions of the metal layer exposed by the patterned hard mask. The thermal anneal may cause the exposed portions of the metal layer to melt and agglomerate into the catalyst nanoparticles, the catalyst nanoparticles having a diameter less than that of the openings in the patterned hard mask.

The method may further comprise forming inner sidewall spacers covering exposed sidewalls of the metal layer and the patterned hard mask. The method may further comprise growing the carbon nanotubes using the catalyst nanoparticles, a diameter of the carbon nanotubes being controlled by a size of the catalyst nanoparticles, filling an oxide over the patterned hard mask, the inner sidewall spacers, the carbon nanotubes and the catalyst nanoparticles, and recessing the oxide to expose the catalyst nanoparticles. The method may further comprise removing the catalyst nanoparticles and etching the carbon nanotubes to form the nanoscale pores. The method may further comprise forming a back chamber in the substrate to expose bottoms of the nanoscale pores. Forming the back chamber in the substrate may utilize at least one of wafer thinning and back side etching processes.

In some embodiments, a semiconductor structure comprises a substrate, an insulator disposed over the substrate, a metal layer disposed over the substrate, a hard mask disposed over the metal layer, the hard mask and the metal layer having two or more patterned openings, inner sidewall spacers disposed on sidewalls of the metal layer and the hard mask in the patterned openings, an oxide layer disposed over the hard mask and filling the patterned openings, and two or more nanoscale pores disposed in the oxide layer in the patterned openings.

The two or more nanoscale pores may comprise circular nanoscale pores having a substantially uniform diameter. The substantially uniform diameter may be 5 nm or less.

The semiconductor structure may further comprise a back chamber in the substrate and the insulator that exposes bottoms of the nanoscale pores.

In some embodiments, a nanoscale pore-based molecule detection device comprises a chamber comprising a conductive solution, first and second electrochemical electrodes in contact with the conductive solution and coupled to a voltage source, and a semiconductor structure disposed in the chamber. The semiconductor structure comprises a substrate, an insulator disposed over the substrate, a metal layer disposed over the substrate, a hard mask disposed over the metal layer, the hard mask and the metal layer having two or more patterned openings, inner sidewall spacers disposed on sidewalls of the metal layer and the hard mask in the patterned openings, an oxide layer disposed over the hard mask and filling the patterned openings, and two or more nanoscale pores disposed in the oxide layer in the patterned openings. The two or more nanoscale pores may comprise circular nanoscale pores having a substantially uniform diameter.

In the description above, various materials and dimensions for different elements are provided. Unless otherwise noted, such materials are given by way of example only and embodiments are not limited solely to the specific examples given. Similarly, unless otherwise noted, all dimensions are given by way of example and embodiments are not limited solely to the specific dimensions or ranges given.

Semiconductor devices and methods for forming same in accordance with the above-described techniques can be employed in various applications, hardware, and/or electronic systems. Suitable hardware and systems for implementing embodiments of the invention may include, but are not limited to, personal computers, communication networks, electronic commerce systems, portable communications devices (e.g., cell and smart phones), solid-state media storage devices, functional circuitry, etc. Systems and hardware incorporating the semiconductor devices are contemplated embodiments of the invention. Given the teachings provided herein, one of ordinary skill in the art will be able to contemplate other implementations and applications of embodiments of the invention.

In some embodiments, the above-described techniques are used in connection with semiconductor devices that may require or otherwise utilize, for example, complementary metal-oxide-semiconductors (CMOSs), metal-oxide-semiconductor field-effect transistors (MOSFETs), and/or FinFETs. By way of non-limiting example, the semiconductor devices can include, but are not limited to CMOS, MOSFET, and FinFET devices, and/or semiconductor devices that use CMOS, MOSFET, and/or FinFET technology.

Various structures described above may be implemented in integrated circuits. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming a semiconductor structure, comprising:
   forming two or more catalyst nanoparticles from a metal layer disposed over a substrate in two or more openings of a hard mask patterned over the metal layer;
   growing two or more carbon nanotubes using the catalyst nanoparticles;
   removing the carbon nanotubes to form two or more nanoscale pores;
   wherein forming the catalyst nanoparticles comprises performing a thermal anneal to form the catalyst nanoparticles from portions of the metal layer exposed by the patterned hard mask;
   forming inner sidewall spacers covering exposed sidewalls of the metal layer and the patterned hard mask;
   growing the carbon nanotubes using the catalyst nanoparticles, a diameter of the carbon nanotubes being controlled by a size of the catalyst nanoparticles;
   filling an oxide over the patterned hard mask, the inner sidewall spacers, the carbon nanotubes and the catalyst nanoparticles; and
   recessing the oxide to expose the catalyst nanoparticles.

2. The method of claim 1, wherein the two or more nanoscale pores comprise circular nanoscale pores.

3. The method of claim 2, wherein the two or more openings in the hard mask have non-uniform size, and diameters of the two or more nanopores are controlled by a size of the carbon nanotubes.

4. The method of claim 2, wherein the diameters of the two or more nanopores are 5 nanometers or less.

5. The method of claim 1, wherein the metal layer comprises at least one of gold, nickel, iron and a nickel-iron alloy.

6. The method of claim 1, wherein the substrate comprises an insulator disposed over a semiconductor material.

7. The method of claim 1, wherein the patterned hard mask comprises a set of oxide pads with gaps between the oxide pads varying in a range of 8 to 12 nanometers.

8. The method of claim 1, wherein the thermal anneal causes the exposed portions of the metal layer to melt and agglomerate into the catalyst nanoparticles, the catalyst nanoparticles having a diameter less than that of the openings in the patterned hard mask.

9. The method of claim 1, further comprising:
   removing the catalyst nanoparticles; and
   etching the carbon nanotubes to form the nanoscale pores.

10. The method of claim 9, further comprising forming a back chamber in the substrate to expose bottoms of the nanoscale pores.

11. The method of claim 10, wherein forming the back chamber in the substrate utilizes at least one of wafer thinning and back side etching processes.

12. The method of claim 1, wherein the thermal anneal is performed at a temperature between 500° C. and 800° C. in an inert atmosphere.

13. The method of claim 1, wherein the inner sidewall spacers comprise one or more of silicon nitride (SiN), silicon oxide ($SiO_x$), and silicon carbide (SiC).

14. The method of claim 1, wherein the inner sidewalls spacers are formed utilizing a sidewall image transfer process.

15. The method of claim 1, wherein growing the carbon nanotubes using the catalyst nanoparticles comprises utilizing a tip-growth model.

16. The method of claim 15, wherein the tip-growth model comprises decomposing a hydrocarbon precursor molecule on top surfaces of the catalyst nanoparticles.

17. The method of claim 16, wherein the hydrocarbon precursor molecule decomposed on the top surfaces of the catalyst nanoparticles comprises diffusing carbon through the catalyst nanoparticles to precipitate the carbon nanotubes out across from bottom surfaces of the metal layer.

18. The method of claim 9, wherein etching the carbon nanotubes to form the nanoscale pores comprises utilizing at least one of an ozone etch and water-assisted etching.

* * * * *